United States Patent
Milster et al.

(10) Patent No.: US 9,072,473 B2
(45) Date of Patent: Jul. 7, 2015

(54) IN-VIVO OPTICAL SENSOR

(75) Inventors: Thomas D. Milster, Tucson, AZ (US);
Kurt R. Denninghoff, Tucson, AZ (US);
Pramod K. Khulbe, Tucson, AZ (US);
Jun Zhang, Tucson, AZ (US)

(73) Assignee: The Arizona board of Regents on Behalf of the University of Arizona, Tucson, AZ (US)

( * ) Notice: Subject to any disclaimer, the term of this patent is extended or adjusted under 35 U.S.C. 154(b) by 327 days.

(21) Appl. No.: 13/430,305

(22) Filed: Mar. 26, 2012

(65) Prior Publication Data

US 2013/0012793 A1    Jan. 10, 2013

Related U.S. Application Data

(60) Provisional application No. 61/465,773, filed on Mar. 24, 2011.

(51) Int. Cl.
*A61B 5/1455* (2006.01)
*A61B 6/00* (2006.01)
*A61B 5/145* (2006.01)

(52) U.S. Cl.
CPC ............... *A61B 5/1455* (2013.01); *A61B 6/00* (2013.01); *A61B 5/14503* (2013.01); *A61B 5/14551* (2013.01)

(58) Field of Classification Search
CPC .................................................. A61B 5/1455
USPC ................................................. 600/310–344
See application file for complete search history.

(56) References Cited

U.S. PATENT DOCUMENTS

| | | | |
|---|---|---|---|
| 3,818,902 A * | 6/1974 | Kinoshita et al. | 600/109 |
| 5,939,709 A | 8/1999 | Ghislain et al. | |
| 6,180,415 B1 | 1/2001 | Schultz et al. | |
| 6,798,511 B1 | 9/2004 | Zhan et al. | |
| 7,016,021 B2 | 3/2006 | Nakajima et al. | |
| 2006/0274611 A1 | 12/2006 | Challener et al. | |
| 2009/0312631 A1* | 12/2009 | Rabinovitz et al. | 600/431 |
| 2009/0326344 A1* | 12/2009 | Meyer | 600/322 |
| 2010/0286674 A1* | 11/2010 | Ben-Yakar et al. | 606/10 |

OTHER PUBLICATIONS

Lyon, et al., "An improved surface plasmon resonance imaging apparatus," Rev. Sci. Instrum. 70, 2076 (1999).
Harke, et al., "Description of a single modular optical setup for ellipsometry, surface plasmons, waveguide modes, and their corresponding imaging techniques including Brewster angle microscopy," Rev. Sci. Instrum. 68, 3130 (1997).

(Continued)

*Primary Examiner* — Eric Winakur
*Assistant Examiner* — Marjan Fardanesh
(74) *Attorney, Agent, or Firm* — McDonnell Boehnen Hulbert & Berghoff LLP

(57) ABSTRACT

An apparatus for determining an optical property of a set of cells is described. The apparatus may include a light source for providing a light signal, a light-conditioning unit configured to condition the light signal, and a diffractive structure. The diffractive structure may be configured to receive the conditioned light signal and produce diffracted light having plasmon-resonance properties and an angular spectrum. The angular spectrum may correspond to the set of cells when the set of cells are within a threshold distance from the diffractive structure. The apparatus further includes a light-collecting unit for collecting the diffracted light.

24 Claims, 10 Drawing Sheets

(56) References Cited

OTHER PUBLICATIONS

Friebel, et al., "Determination of the complex refractive index of highly concentrated hemoglobin solutions using transmittance and reflectance measurements," Journal of BM Optics (2005), 10(6):064019-1-5.

Kugeiko, et al., "Determination of the refractive index of spherical erythrocytes of human blood in the range of 0.3-1.2 microns" Journal of Applied Spectroscopy, (2007), 74(3):425-429.

Giebel, "Imaging of Cell/Substrate Contacts of Living Cells with Surface Plasmon Resonance Microscopy" Biophysical Journal, (1999)vol. 76, Issue 1, pp. 509-516.

Chen, et al., "Properties of induced polarization evanescent reflection with a solid immersion lens (SIL)," Optics Express, vol. 15, Issue 3, pp. 1191-1204 (2007).

Ghosh, et al., "Simultaneous determination of size and refractive index of red blood cells by light scattering measurements," App Phys Lett (2006), 88:084101.

Zhang, et al., "Surface-plasmon microscopy with a two-piece solid immersion lens: bright and dark fields," Applied Optics, vol. 45, Issue 31, pp. 7977-7986 (2006).

Homola, et al., "Surface plasmon resonance sensors: Review" Sensors and Actuators B, (1999), 54:3-15.

* cited by examiner

IN-VIVO OPTICAL SENSOR

CROSS-REFERENCE TO RELATED APPLICATIONS

The present application claims priority under 35 U.S.C. §119(e) to U.S. Provisional Patent Application Ser. No. 61/465,773, filed Mar. 24, 2011, which is incorporated herein by reference in its entirety.

BACKGROUND

Unless otherwise indicated herein, the materials described in this section are not prior art to the claims in this application and are not admitted to be prior art by inclusion in this section.

Delivery of oxygen to a living tissue and the amount of oxygen used by living tissues can be indispensable pieces of information for medical personnel, such as doctors. The body of a living creature receives oxygen through blood. Therefore, monitoring the amount of oxygen in the blood is extremely important, especially during surgery, in intensive care units (ICU), or in emergency-care situations, among other examples.

In some techniques for determining the amount of oxygen in the blood, blood is first drawn from a patient, and then transported to a device, such as a co-oximeter, to determine a blood-oxygen level. However, the time required to draw blood and determine the blood-oxygen level in accordance with such techniques may result in a delay that is unacceptable in situations such as, among other examples, post-cardiac surgery, or treatment of head trauma, where brain tissue has only minutes to live after the blood oxygen supply is depleted. As such, what is needed is a device that reliably provides medical personnel with substantially immediate and accurate information about the amount of oxygen in the blood.

SUMMARY

The present disclosure describes apparatuses and methods for reliably determining accurate information regarding the optical properties of a given medium. In accordance with certain embodiments, the apparatuses and methods may be used to determine the optical properties of red blood cells and, thereby, reliably and accurately determine the amount of oxygen in blood. Further, in accordance with certain embodiments, the apparatuses and methods may be utilized in-vivo and thereby provide real time, immediate, information regarding blood-oxygen levels.

A first embodiment of the disclosed apparatuses and methods may take the form of an apparatus for determining an optical property of a set of cells that includes (a) a light source for providing a light signal, (b) a light-conditioning unit configured to condition the light signal, (c) a diffractive structure configured to (i) receive the conditioned light signal and (ii) produce a diffracted light signal having plasmon-resonance properties and an angular spectrum, the angular spectrum corresponding to the set of cells when the set of cells are within a threshold distance from the diffractive structure, and (d) a light-collecting unit for collecting the diffracted light signal.

In an aspect of the first embodiment, the light source may include a laser that is coupled to the light-conditioning unit. In another aspect of the first embodiment, the light-collecting unit may include a camera, as well as a lens positioned between the diffractive structure and the camera. In yet another aspect of the first embodiment, the light grating unit may include one or more of a plasmon-resonance layer, an adhesion layer, and a protective layer. In yet another aspect of the first embodiment still, one or more elements of the apparatus may be contained within a catheter to help facilitate the placement of the apparatus inside of an individual.

A second embodiment of the disclosed apparatuses and methods may take the form of a method for determining an optical property of a set of cells that includes (a) projecting a light signal on a diffractive structure, where the diffractive structure is configured to (i) receive the light signal and (ii) produce a diffracted light signal having plasmon resonance properties and an angular spectrum, the angular spectrum corresponding to the set of cells when the set of cells are in contact with the diffractive structure, (b) detecting the diffracted light signal, and (c) determining the optical property of the set of cells based on the detected diffracted light signal.

In a third embodiment, a non-transitory computer readable storage medium may contain instructions that cause a computing system to perform the method for determining an optical property of a set of cells.

A fourth embodiment of the disclosed apparatuses and methods may take the form of a method for determining an oxygen saturation level in an individual that includes (a) exposing a first side of a diffractive structure to a blood stream of the individual such that the first side of the diffractive structure is in contact with a set of red blood cells from the blood stream, wherein the diffractive structure is configured to (i) receive a light signal on a second side of the diffractive structure and (ii) produce a diffracted light signal having plasmon resonance properties and an angular spectrum, the angular spectrum corresponding to the set of red blood cells, (b) projecting the light signal on the second side of the diffractive structure, (c) detecting the diffracted light signal, and (d) determining the oxygen saturation level based on the detected diffracted light signal.

In a fifth embodiment, a non-transitory computer readable storage medium may contain instructions that cause a computing system to perform the method for determining an oxygen saturation level in an individual.

These as well as other aspects, advantages, and alternatives will become apparent to those of ordinary skill in the art by reading the following detailed description, with reference where appropriate to the accompanying drawings. Further, it should be understood that the disclosure provided in this summary section and elsewhere in this document is intended to describe the invention by way of example only and not by way of limitation.

DETAILED DESCRIPTION

Figure 1:
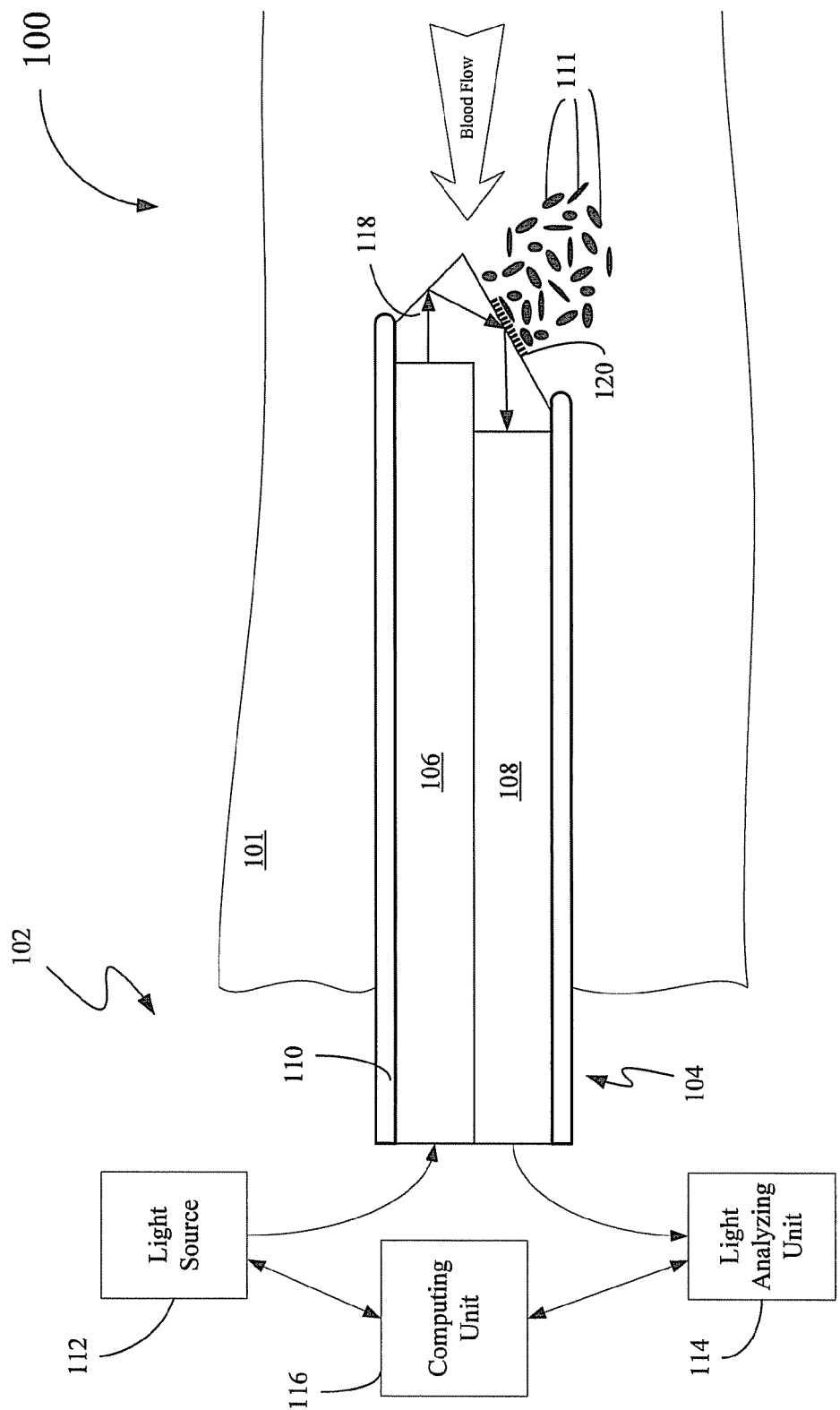
FIG. 1 is a schematic diagram illustrating an example embodiment of an apparatus for in-vivo detection of optical properties of cells.

In the following detailed description, reference is made to the accompanying figures, which form a part thereof. In the figures, similar symbols typically identify similar components, unless context dictates otherwise. The illustrative embodiments described in the detailed description and figures are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

1. Introduction

Oxygen is an essential part of cellular metabolism. A percentage of oxygen that can be carried by hemoglobin in red blood cells (RBCs) may be referred to as oxygen saturation. Existing techniques for measuring oxygen saturation involve a number of devices, such as with a co-oximeter, a pulse oximeter, or a fiberoptic reflection spectroscopy.

A typical co-oximeter utilizes a multiple-wavelength light source that transmits through a sample of hemolysed blood, where RBC membranes are shattered with ultrasound in order to make the hemolysed blood sample homogeneous, once drawn from a patient. The hemolysed blood sample is placed such that a light beam passes through it. Since co-oximeters are configured to make in-vitro measurements, they provide accurate saturation readings only once the blood sample is drawn from the patient.

A typical in-vivo pulse oximeter may include two or three light emitting diodes (LEDs) positioned near the skin of a patient. Each LED may emit a different color. For two-color devices, one color may be red (660 nm) and the other color may be just beyond the visible light (940 nm) in the near infrared (NIR) region. The LED light transmits through the skin and into finger tissue of the patient, and scatters off the finger bone, tissue, and RBCs. Eventually, some of the light gets to the detector and is converted into an electrical signal. The amount of light detected depends on many factors, such as the amount of blood and its absorption, skin pigmentation, bone characteristics, etc.

In-vivo pulse oximeters are configured to take advantage of arterial pulsation, where during a cardiac cycle the arteries contain more blood during a systole (high pressure) period than during a diastole (low pressure) period. This effect does not occur in veins or bone or other tissue. Therefore, the alternating part of the detected signal is due to absorption in the additional amount of arterial blood in the region. Since the relative absorption switches between red and NIR wavelengths, it is relatively straightforward to approximate arterial functional oxygen saturation from measurements of the alternating detector signal. Normal values of arterial functional oxygen saturation are between 90% and 97.5%, and are nearly uniform throughout the arterial system. However, there are many sources of error in in-vivo pulse oximeters, and accuracy cannot be reliably determined at less than 70% arterial functional oxygen saturation.

A typical fiberoptic in-vivo reflection oximeter is, in some respects, similar to the pulse oximeter, because it uses two or three wavelengths of light and measures the scattered reflected light on a detector, albeit through a fiberoptic catheter cable. Typically, two wavelengths (red and NIR) are launched into the proximal end of the fiber outside of the patient's body. Light travels down one optic fiber and illuminates blood inside a vein. RBCs and other components scatter light back toward a collection optic fiber that transmits the light to a detector. Amplitudes of the reflected signals are processed along with calibration data in order to estimate oxygen saturation in the vein. In addition to scattering issues due to size and concentration of RBCs, a significant problem with fiberoptic in-vivo reflection oximeters is measurement drift as a function of time, which requires periodic recalibration.

Accordingly, as described herein, an example apparatus that provides improved accuracy of measurements of optical properties of RBCs, may be configured as an internal probe that can be placed directly in the blood stream of a patient to measure optical properties. The optical properties may correspond to oxygen saturation levels of individual cells, such as RBCs, that come in contact with the probe or come within a threshold distance from the probe. In one embodiment, the example apparatus is a fiber-coupled probe configured to measure optical properties of individual cells. The optical properties of an individual cell are sensed by a plasmonic interaction between an integral illuminated diffractive structure, such as a grating, and the individual cell. The example fiber-coupled probe is also configured to enable a self-calibration. In one embodiment, the example fiber-coupled probe includes a calibrated in-vivo blood oximeter that is configured to be accurate to about 1% oxygen saturation, and includes a sensing surface that helps detect refractive index of individual red blood cells.

In an embodiment other types of cells, including other types of blood cells, such as, in addition to erythrocytes (red blood cells), leukocytes (white blood cells), and platelets (thrombocytes), may be analyzed as well. The cells described above are described for purposes of example and explanation only, and should not be taken to be limiting. Other types of cells may be analyzed as well.

In an embodiment, one or more additional properties of cells may be analyzed based on the optical analysis including, for example, the dipole moment and polarization of the membrane and various mechanical properties of the membrane, which may be due to changes in the lipid bilayer surrounding mammalian cells. These changes can influence the distribution of proteins in the membrane and the transport of ions in and out of the cell through the membrane, and are therefore of interest in a variety of applications. The properties described above are described for purposes of example and explanation only, and should not be taken to be limiting. Other types of properties may be analyzed as well.

2. Example Apparatus a. Overview of Example Apparatus

As noted above, a first embodiment of the disclosed apparatus may take the form of an apparatus for determining an optical property of a set of cells that includes (a) a light source for providing a light signal, (b) a light-conditioning unit configured to condition the light signal, (c) a diffractive structure configured to (i) receive the conditioned light signal and (ii) produce a diffracted light signal having plasmon-resonance properties and an angular spectrum, the angular spectrum corresponding to the set of cells when the set of cells are within a threshold distance from the diffractive structure, and (d) a light-collecting unit for collecting the diffracted light signal.

The light source for providing the light signal may take the form of any suitable light source. In an embodiment, the light source may be a multiple-wavelength light source. For instance, the light source may be a multiple-wavelength laser, a multiple-wavelength light emitting diode (LED) array, a super luminescent LED (SLED), a thermal source, or another light source arranged to provide light at desired wavelengths. As will be described further below with respect to the light-conditioning unit, a wavelength filter may be used to select specific wavelengths provided by the light source. It should be understood that the examples of the light source provided herein are provided for purposes of example and explanation only and should not be taken to be limiting. Other examples may exist as well.

The light-conditioning unit configured to condition the light signal may take the form of any suitable light-conditioning unit. As a general matter, the light-conditioning unit may be arranged so as to focus, concentrate, and/or filter, the light signal provided by the light source. In an embodiment, the light-conditioning unit may include any suitable components for conditioning the light signal including a polarizer, a lens (e.g. a graded index lens), an aperture, a slab waveguide, a computer-generated hologram, and/or a diffractive optical element, among other examples. It should be understood that the examples of the light-conditioning unit provided herein are provided for purposes of example and explanation only and should not be taken to be limiting. Other examples may exist as well.

The diffractive structure may take the form of any suitable diffractive structure. Generally, the diffractive structure may be configured to (i) receive the conditioned light signal and (ii) produce a diffracted light signal having plasmon-resonance properties and an angular spectrum. As discussed further below, the angular spectrum of the produced diffracted light will correspond to the set of cells when the set of cells are within a threshold distance from the diffractive structure. Accordingly, the diffractive structure may include a grating unit having a periodic structure of protrusions that have a periodicity that is smaller than an average length of the cells. In this way, light that is incident on the diffractive structure will cause a condition of plasmon resonance along the surface of the diffractive structure, and the set of cells within the threshold distance from the diffractive structure will cause the diffractive light to have an angular spectrum corresponding to optical properties of the set of cells.

In an embodiment, the grating unit of the diffractive structure may include a plasmon-resonance layer made up of any suitable material that may form the plasmon resonance. For instance, the plasmon-resonance layer may be made of silver, however this is not required. Other examples of the plasmon-resonance layer may exist as well.

In addition to the plasmon-resonance layer, the grating unit may include one or more of an adhesion layer and a protective layer. The adhesion layer may be made up of any suitable material that adheres the grating unit to a surface to which the diffractive structure is attached (referred to below as a "sensing surface"). For instance, the adhesion layer may be made of chromium, however this is not required. Other examples of the adhesion layer may exist as well. The protective layer may be made up of any suitable material that protects the plasmon-resonance layer. For instance, the protective layer may be made of silicon dioxide, however this is not required. Other examples of the protective layer may exist as well. Example, alternative, embodiments of the grating unit are discussed further below.

The grating unit may have a periodic structure. Further, the periodic structure may have a periodicity that is smaller than an average length of the cells within the threshold distance from the diffractive structure. Alternatively, the grating unit may have a non-periodic structure so long as an average length of the cells within the threshold distance from the diffractive structure is greater than a plurality of repeated protrusions of the grating unit.

Further, the diffractive structure may be arranged to have any desired diffraction order. In an embodiment, the diffractive structure may have a (−1) diffraction order, however this is not necessary. Other examples of the diffraction order of the diffractive structure may exist as well.

The light-collecting unit for collecting the diffracted light signal may take the form of any suitable light-collecting unit. As a general matter, the light-collecting unit may be arranged so as to image the diffracted light so that the spectrum of the diffracted light may be analyzed. In an embodiment, the light-collecting unit may take the form of a camera, such as a charge coupled device (CCD) camera. Other examples of suitable cameras may exist as well. Further, the light-collecting unit may be arranged so as to condition the diffracted light. Thus, in an embodiment, the light-collecting unit may include any suitable components for conditioning the diffracted light including a polarizer, a lens (e.g., a graded index lens), and/or an aperture, among other examples. In a particular embodiment, the light-collecting unit may include a lens positioned between the diffractive structure and the camera. It should be understood that the examples of the light-collecting unit provided herein are provided for purposes of example and explanation only and should not be taken to be limiting. Other examples may exist as well.

It should be understood that the above examples describe various example embodiments for purposes of example and explanation. Many example embodiments of the apparatus described herein exist, some of which are discussed in more detail below, with reference to the figures.

b. First Example In-Vitro Optical Sensor

Aspects of an example in-vitro optical sensor are described below. Certain aspects of the example optical sensor described below are not necessarily meant to be limiting. Further, other aspects may be utilized, and other changes may be made, without departing from the spirit or scope of the subject matter presented herein. It will be readily understood that certain aspects illustrated in the figures, can be removed, arranged, substituted, combined, separated, and/or designed in a wide variety of different configurations.

Referring to FIG. 1, an example embodiment 100 of an apparatus 102 for in-vivo detection of optical properties of individual cells is shown. Apparatus 102 includes a structure 104 having a light-conditioning unit 106 and a light-collecting unit 108 surrounded by a jacket 110. Hereafter, apparatus 102 will be referred to as a fiber-coupled probe, which further includes a light source 112, a light-analyzing unit 114, and a computing unit 116. At one proximal end of light-conditioning unit 106 and of light-collecting unit 108, fiber-coupled probe 102 includes a molded prism 118, and a diffractive structure 120 coupled to an external surface of molded prism 118. In an embodiment, jacket 110 may be a catheter.

As those skilled in the art will appreciate, catheters typically have multiple lumens, or devices that perform functions. In accordance with the present disclosure, one lumen in a catheter could include the fiber-coupled probe, and other relevant components, of the apparatus described herein. For purposes of example and explanation, other lumens included in the same catheter may include a temperature probe or an imaging fiber. Thus, the fiber-coupled probe, as well as other relevant components that may be included within a catheter, may be designed, arranged, or otherwise configured to fit into a standard lumen cavity of a common catheter.

It is of further note that according to some catheter-lumen designs, the lumen is mechanically movable within the catheter. That is the lumen is movable towards and away from both the proximal and distal ends of the catheter. Accordingly, the fiber-coupled probe described herein may be designed, arranged, or otherwise configured to be mechanically moved within the catheter (i.e., moved towards and away from the proximal and distal ends of the catheter).

Placement of the fiber-coupled probe (e.g., by way of a catheter) within an individual is discussed further below.

It should be understood that while diffractive structure 120 is shown as coupled to molded prism 118, this is not necessary so long as the diffractive structure is configured to (i) receive the conditioned light signal and (ii) produce a diffracted light signal having plasmon-resonance properties and an angular spectrum. The configuration of diffractive structure 120 shown in FIG. 1 is but one possible configuration, and other configurations may exist as well.

In one embodiment, light source 112 is configured to produce a light signal having a plurality of wavelengths (e.g., substantially all wavelengths within a given spectrum), which may be provided to light-conditioning unit 106. Alternatively, light source 112 may be a laser or LED array that produces a light signal having a specific number of wavelengths. When light source 112 is a laser, light-conditioning unit 106 may be a multiple-mode optical fiber. Light-analyzing unit 114 may be integrated in whole, or in part with light-collecting unit 108. In general light-analyzing unit 114 is configured to receive the light signal from light-collecting unit 108 for identifying wavelengths of the received light signal, and for imaging individual cells that impacted the reflection or diffraction of the received light signal.

Light-analyzing unit 114 may include a camera, which may be a charge coupled device (CCD). Alternatively, or additionally, light-analyzing unit 114 may include CMOS detector arrays, HgCdTe detector arrays, arrays of intrinsic or intrinsic semiconductor detectors, bolometer or pyroelectric arrays, other photoconductive or photovoltaic arrays, metal-insulator semiconductor arrays, and/or capacitive or resistive bolometer arrays, among other examples. It should be understood that the examples of the light-analyzing unit provided herein are provided for purposes of example and explanation only and should not be taken to be limiting. Other examples may exist as well.

In one embodiment, each of light-conditioning unit 106 and light-collecting unit 108 includes an optical fiber. As such, light-conditioning unit 106 is configured to condition and provide a light signal received from light source 112 to molded prism 118, which in turn directs the conditioned light signal onto a sensing surface 122 of light diffractive structure 120, as shown in FIG. 3.

Figure 2:
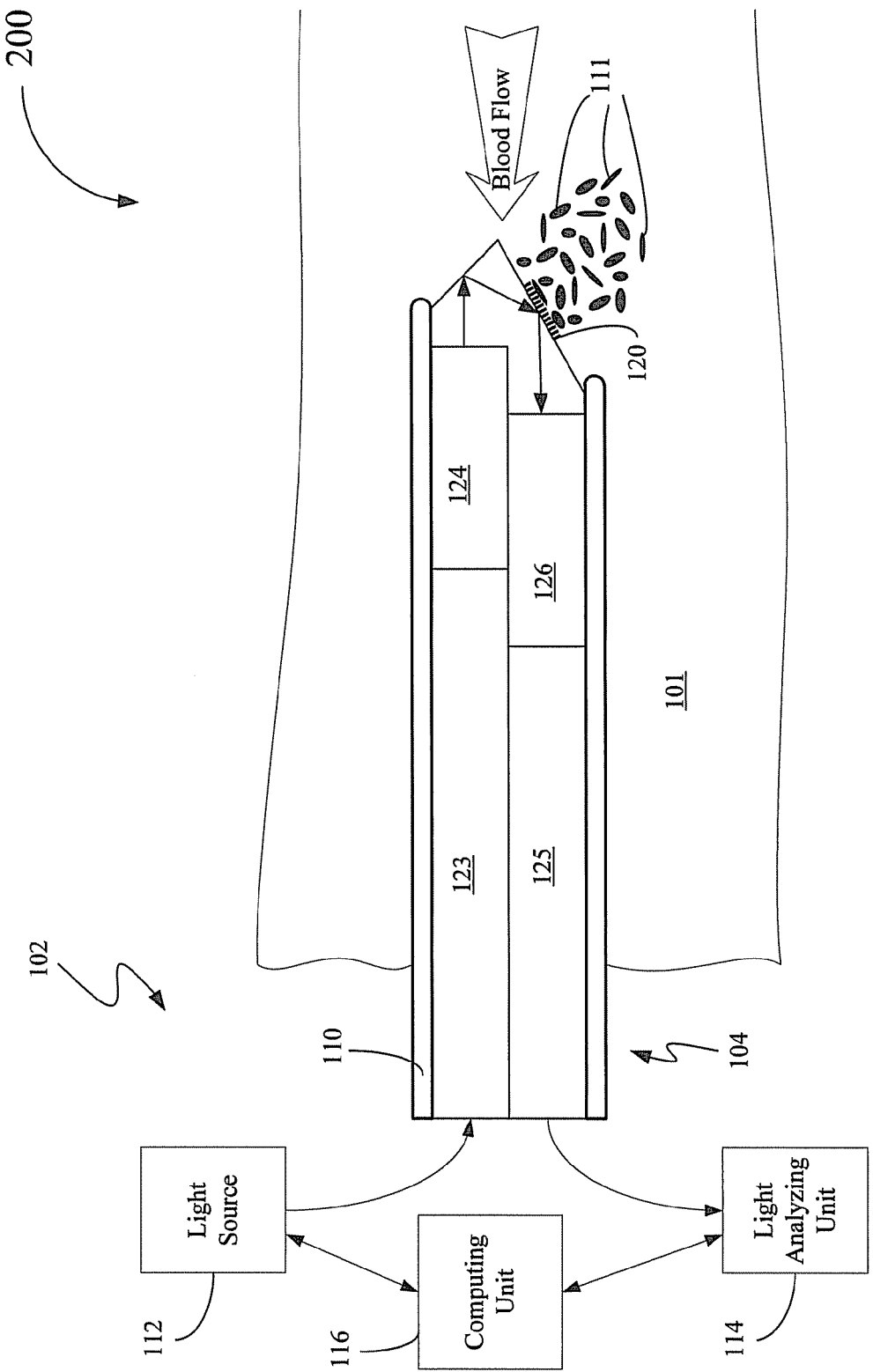
FIG. 2 is a schematic diagram illustrating another example embodiment of an apparatus for in-vivo detection of optical properties of cells.

Now referring to FIG. 2, another example embodiment 200 of fiber-coupled probe 102 is illustrated. As shown, each of light-conditioning unit 106 and light-collecting unit 108 includes a graded index lens 124 and 126, respectively, coupled to corresponding optical fibers 123 and 125. Graded index lens 124 is configured to transfer the light signal to molded prism 118, and graded index lens 126 is configured to transfer diffracted or reflected light signal from sensing surface 122 to optical fiber 125. As such, optical fiber 123, graded index lens 124, and molded prism 118 provide an optical path for the source light to reach sensing surface 122 (as shown in FIG. 3). Further, molded prism 118, graded index lens 126, and optical fiber 125 provide an optical path for the reflected light signal to reach light-analyzing unit 114.

As noted above, jacket 110 of the fiber-coupled probe 102 shown in FIGS. 1 and 2 may be a catheter. Accordingly, fiber-coupled probe 102 may be inserted into an artery or a vein 101 of a person or an animal. Upon insertion, a venous blood flow directed towards molded prism 118 may provide a hemodynamic pressure so that individual cells, such as RBCs 111, may come into serial contact with, or in close proximity to, sensing surface 122. Further, molded prism 118 may be reconfigured shape-wise to work in conditions where blood flows along a different direction relative to fiber-coupled probe 102 from that shown in FIGS. 1 and 2. Alternatively, fiber-coupled probe 102 may be used to analyze optical properties of cells moving or floating in a liquid other than blood or plasma. As noted above, properties of mammalian cell membranes may also be analyzed, including the polarization and dipole moment.

Figure 3:
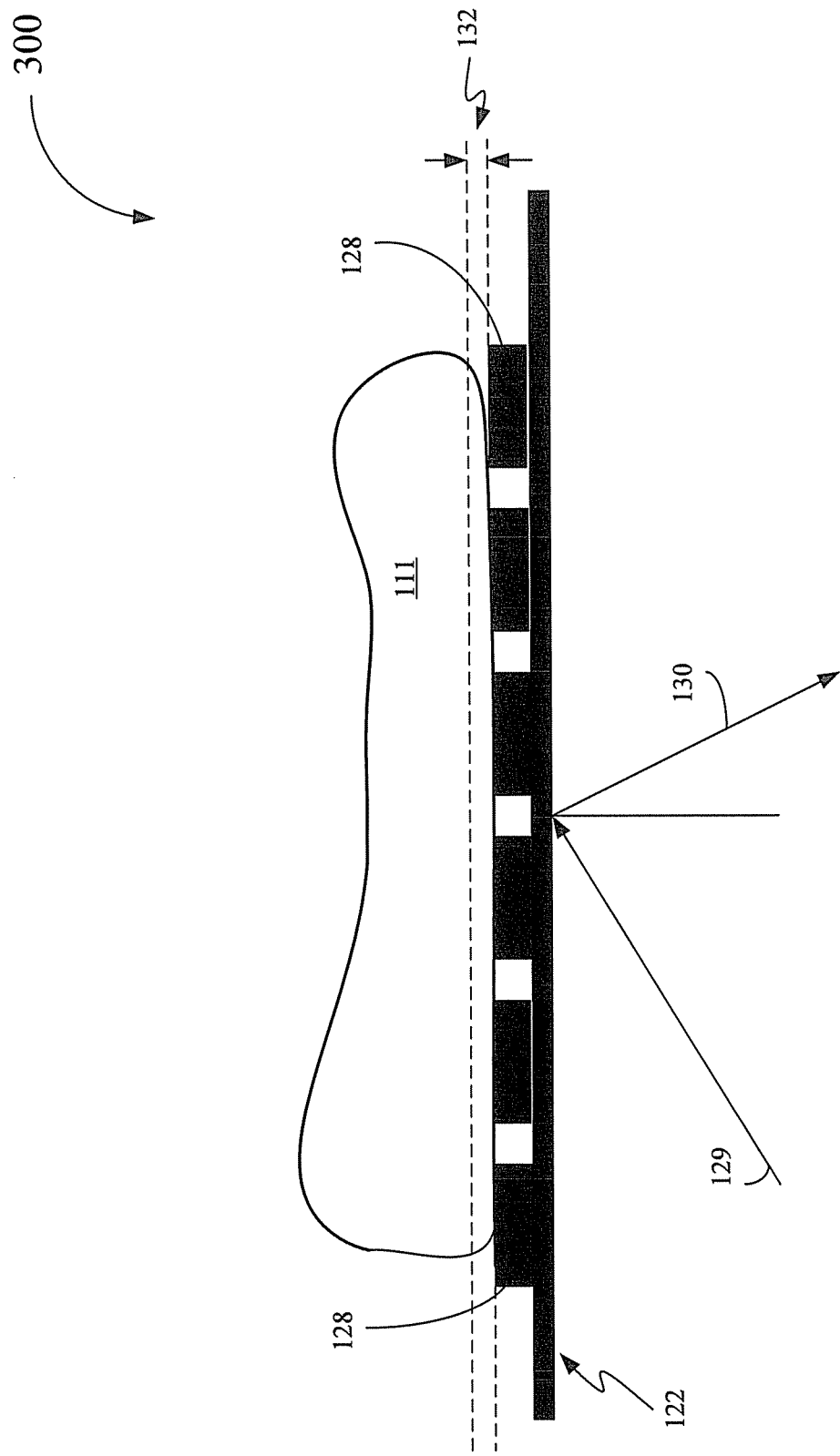
FIG. 3 is a schematic diagram of a diffractive structure of the apparatus of FIG. 1.

Now referring to FIG. 3, an example embodiment of a cross-section of diffractive structure 120 of fiber-coupled probe 102 is shown. For the sake of clarity in description of fiber-coupled probe 102, hereafter the medium in which fiber-coupled probe 102 is immersed during operation may be described as blood and the individual cells may be described as RBCs 111. However, this is only for purposes of example and explanation, and should not be taken to be limiting.

As stated above, diffractive structure 120 is positioned so as to be in contact with an external surface of molded prism 118. As such, during operation, sensing surface 122 is positioned between the external surface of molded prism 118 and blood containing RBCs 111. In one embodiment, sensing surface 122 includes a grating unit 128 on a surface facing away from molded prism 118 that is configured to produce a plasmon resonance for certain combinations of RBC refractive indices and incident light angles.

However, as noted above, it should be understood that while diffractive structure 120 is shown as coupled to molded prism 118, this is not necessary so long as the diffractive structure is configured to (i) receive the conditioned light signal and (ii) produce a diffracted light signal having plasmon-resonance properties and an angular spectrum. The configuration of diffractive structure 120 shown in FIG. 3 is but one possible configuration, and other configurations may exist as well.

As shown in FIG. 3, a diffracted light signal 130 from grating unit 128 is directed to light-collecting unit 108. Diffracted light signal 130 may not return at the same angle $\theta_r$ as that of incident light signal 129 provided by light source 112 via light-conditioning unit 106 because grating unit 128 may be configured to redirect part of the energy of incident light signal 129 into a plurality of diffracted orders. In one embodiment, as shown in FIG. 3, grating unit 128 is configured to have diffracted light signal 130 with a "−1" diffraction order return through light-collecting unit 108. Alternatively, any other suitable diffraction order may be selected for diffracted light signal 130. Moreover, in one embodiment, only selected diffraction orders may be allowed to pass from molded prism 118 to light-collecting unit 108 by selecting and positioning therebetween an appropriate aperture (not shown).

During operation, when an individual RBC 111 is in contact or in proximity of grating unit 128, and a refractive index of the individual RBC 111 is near resonance with grating unit 128, an amount of diffracted light signal 130 from that area may be reduced. Further, an amount of diffracted light signal 130 may be higher in areas surrounding the contact area. Due to an exponential decay of evanescent energy next to sensing surface 122, a sensing region 132 may be confined to a certain height above grating unit 128, such as a height of about 0.1 μm. As such, RBCs 111 not in sensing region 132 may not have any impact, or may not affect, diffracted light signal 130. In other words, the angular spectrum of the diffracted light may correspond to a set of cells that are within a threshold distance (or height) from the diffractive structure.

Figure 4:
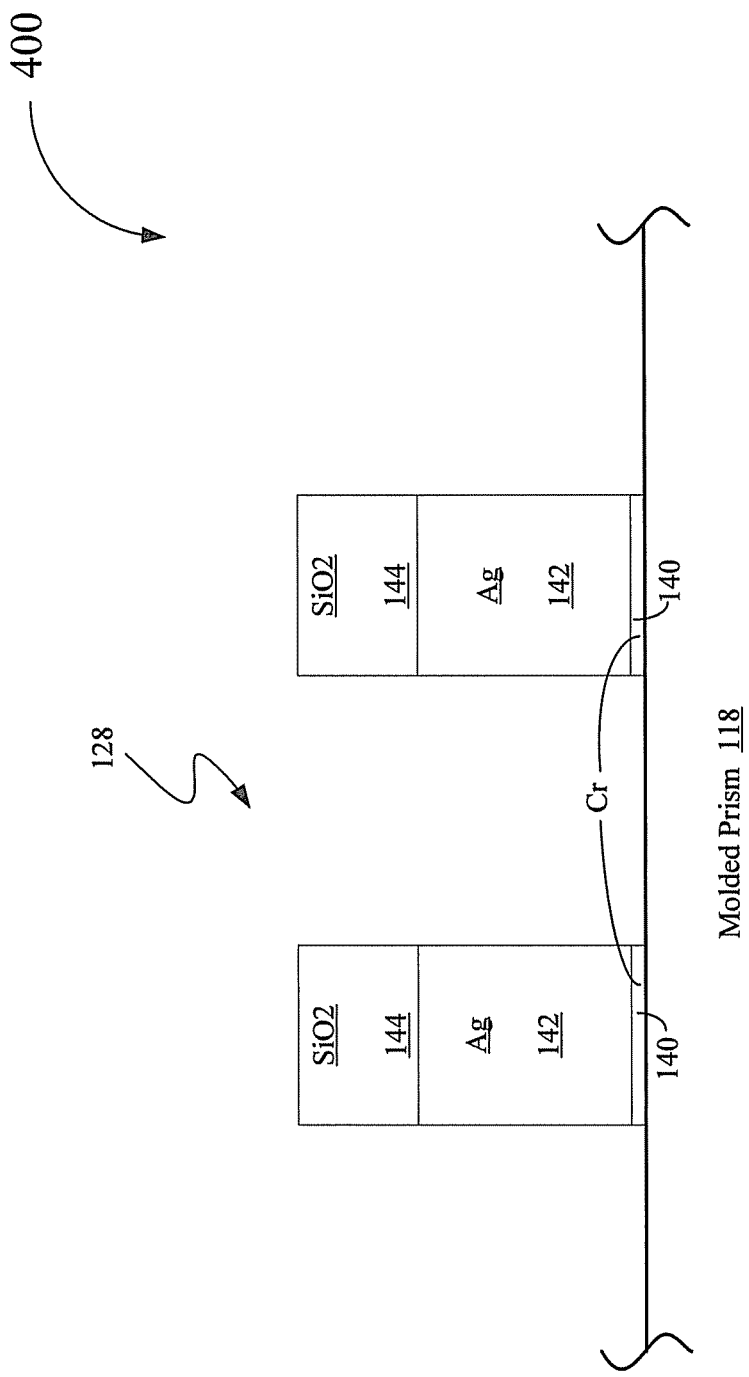
FIG. 4 is a schematic diagram of a cross-section of the diffractive structure of FIG. 3.

Now referring to FIGS. 3 and 4, in one embodiment, grating unit 128 may be configured to have a periodic design. The periodicity of the design may be arranged such that an average length or an average thickness of an individual RBC 111 (or other cell of interest) is substantially longer than that of a period of the design. That is, any microscopic region of grating unit 128 that may come in contact with an individual RBC 111 may have an average length or average thickness that is multiple periods of the periodic design. Alternatively, grating unit 128 need not have a strictly periodic design, so long as an individual RBC 111 may cover a plurality of repeated protrusions of grating unit 128.

With respect to an embodiment including a non-periodic grating unit, a slightly curved grating unit may produce a focusing effect in the diffracted light, which might eliminate or reduce the complexity of some other optical components in the device. The grating unit could also consist of semi-periodic structures, where one region of the grating unit has a periodicity tuned to one illuminating wavelength and cell property, and another region of the grating has a second periodicity tuned to a different wavelength or cell property.

As noted above, hemodynamic pressure may cause RBCs 111 to serially contact grating unit 128. Moreover, since a cardiac cycle is relatively slow, e.g., from about 0.5 second to about 1 second, compared to a time, e.g. about 1/30 sec, required to make an optical-property measurement, RBCs 111 are essentially motionless during the time required to make the optical-property measurement. Thus, light diffractive structure 120 is configured to receive conditioned light signal 129 and to produce diffracted light signal 130 having plasmon-resonance properties and an angular spectrum, which may correspond to a set of individual cells when they are in contact with, or within a threshold distance from, diffractive structure 120.

Still referring to FIG. 4, grating unit 128 is shown to be periodic along sensing surface 122 with an example period of about 2 μm. A typical individual RBC 111 has a length equal to about 8 μm, and so the length of four grating periods as shown in FIG. 4 is equal to about the length of the individual RBC 111.

In one embodiment, grating unit 128 may be fabricated by standard lithographic techniques and may include a plurality of layers. As shown, grating unit 128 includes a bottom adhesion layer 140 made of chromium (Cr) and may be approximately 0.005 μm thick. A middle layer 142, formed on adhesion layer 140, may be made of silver (Ag) to form the plasmon resonance, and may be approximately 0.065 μm thick. Grating unit 128 may also include a top layer 144 made of silicon dioxide ($SiO_2$), which is a protective layer and is approximately 0.030 μm thick. Alternatively, adhesion layer 140, middle layer 142, and top layer 144 made be formed of any other suitable minerals or compounds. The specific sizes and materials discussed above with respect to adhesion layer 140, middle layer 142, and top layer 144 are for purposes of example and explanation only and should not be taken to be limiting. Other suitable examples, arrangements, and/or configurations of grating unit 128 may exist.

For example, middle layer 142 may be made from aluminum (Al) or gold (Au). Top layer 144 may be made from titanium dioxide ($TiO_2$) or magnesium dioxide ($MgO_2$). When various materials are used in these layers, thicknesses and period may be adjusted properly to yield the plasmon resonance condition at the appropriate wavelength. The top layer 144 and/or adhesion layer 140 may not be necessary, depending on the wavelength and materials for the middle layer and the grating substrate. Further, the middle layer 142 may be an engineered metamaterial specifically designed for a certain wavelength and cell property. Again, other suitable examples, arrangements, and/or configurations of grating unit 128 may exist.

Sensing surface 122 may contain additional areas possessing known refractive indices. These additional areas may serve as reference indicators for the calibration of fiber-coupled probe 102. One of these additional area may include a low-index material, such as magnesium fluoride (MgF2) that has a refractive index n=1.38, and another area may consist of a higher-index material, such as silicone dioxide ($SiO_2$) that has a refractive index n=1.46.

As noted above, due to hemodynamic pressure, RBCs 111 may come into serial contact with sensing surface 122, and may move along its length until they are off of the sensing portion of sensing surface 122. In one embodiment, computing unit 116 may be configured to identify an individual RBC 111 based on its corresponding diffracted light signal 130, measure its optical property, such as its oxygen saturation, and track its movement on sensing surface 122 so that measurements are not duplicated for the same individual RBC 111. Once computing unit 116 has repeated this identification, measurement, and tracking process for a certain number of RBCs 111, their respective measured optical properties may be stored and used to determine a mean and variance of the measured optical properties for these RBCs 111 over a certain time interval.

Figure 5:
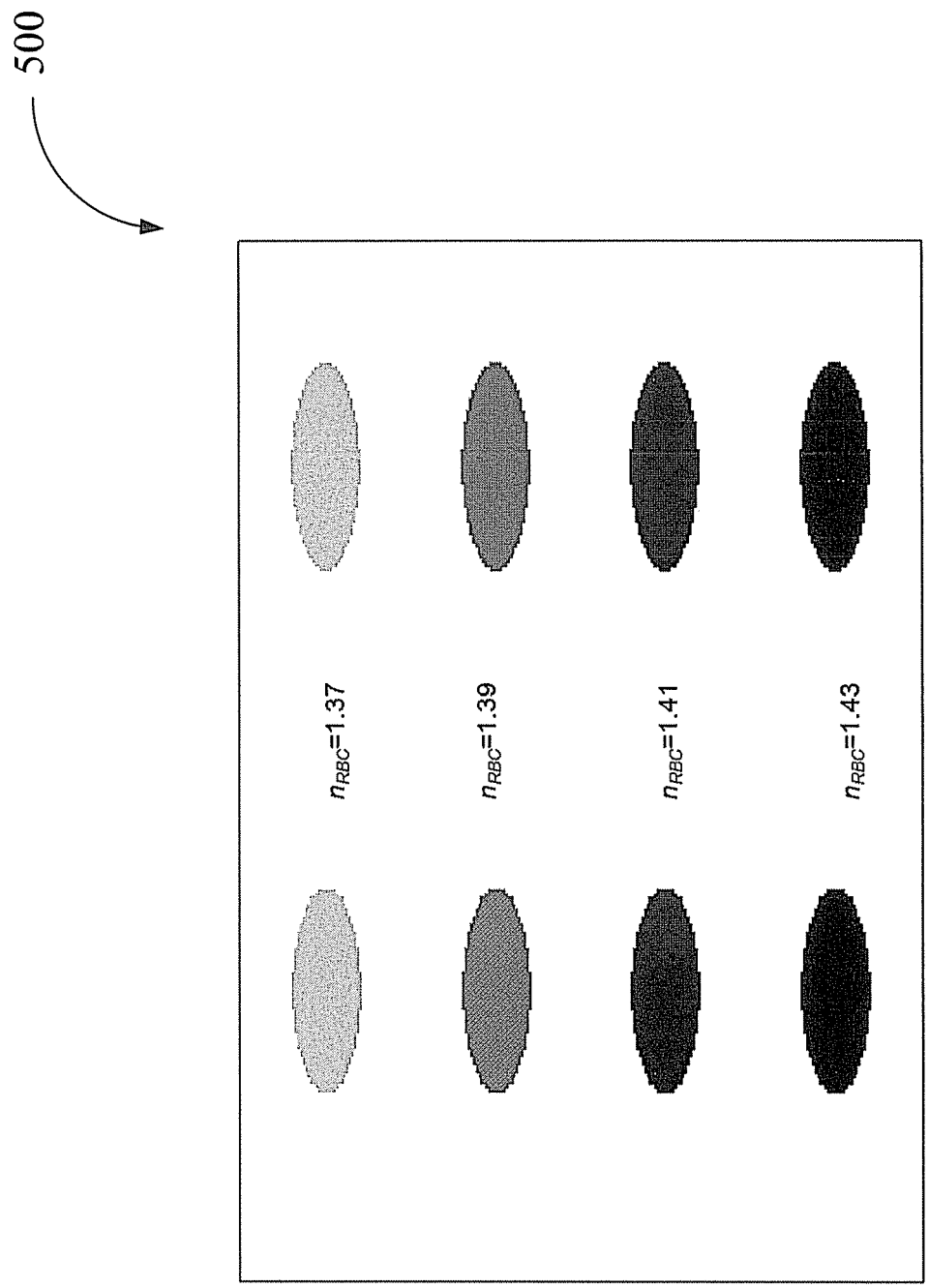
FIG. 5 is a schematic diagram illustrating a plurality of red blood cells (RBCs) having different refractive indices.

As known to one of ordinary skill in the art, components of an individual RBC 111, such as oxygen-depleted (reduced) hemoglobin (Hb), fully saturated oxyhemoglobin ($HbO_2$), carboxyhemoglobin (COHb), and methemoglobin (MetHb), attenuate light differently at different wavelengths. Further, as shown in FIG. 5, various RBCs may have varying refractive indices. The oxygen saturation is known to be defined by the following formula: Oxygen Saturation=$HbO_2$/(Hb+$HbO_2$). Further, dysfunctional hemoglobins, like COHb and MetHb, typically do not support the transport of oxygen and only a few percent of total hemoglobin. As such, an oxygen-saturation level of an individual RBC 111 can be determined based on a measured amount of oxygen-depleted hemoglobin and a measured amount of saturated oxyhemoglobin using the above formula and corresponding detected wavelengths of diffracted light signal 130.

Accordingly, fiber-coupled probe 102 is a device that is configured to measure optical properties of cells, such as RBCs, in proximity to a diffractive structure of fiber-coupled probe 102 based on plasmonic resonance. Further, fiber-coupled probe 102 can be configured to work as an intravenous catheter probe.

b. Second Example In-Vitro Optical Sensor

As noted above, the example in-vitro optical sensor described above with respect to FIGS. 1-3 is but one example configuration of the in-vitro optical sensor described herein. Other example configurations may exist as well.

For example, and as noted above, the light-conditioning unit could include a slab waveguide. In such a case, for example, the light source may be one or more laser diodes bonded to couple light into the slab waveguide. Further, the top of the waveguide may be arranged to serve as the sensing surface. After interaction with the sensing surface, the diffracted light signal, having plasmon resonance properties and an angular spectrum, may be directed through the bottom of the waveguide to the light-analyzing unit. According to this example, the light-conditioning unit is integrated with the light-collecting unit.

This configuration, or any of the other configurations described herein, of the optical sensor may be relatively energy efficient and operate autonomously inside the body without a direct mechanical linkage to the computing unit. That is, a miniaturized battery or electromagnetically coupled power source may be used to drive the light source and light-analyzing unit (e.g., CCD). Information from the light-analyzing unit derived from the diffracted light having surface plasmon properties could be sent via wireless circuit to a computing device. In this way, a doctor could implant the sensor within a patient and continuously monitor properties of cells within the body without the need for mechanical linkage of the optical sensor to a computing unit. The computing unit could be worn on the patient and alert the patient or physician when properties of the cells being monitored fall outside of a predetermined range.

Other examples and other embodiments of the optical sensor described herein may exist as well.

3. Example Methods

Figure 6:
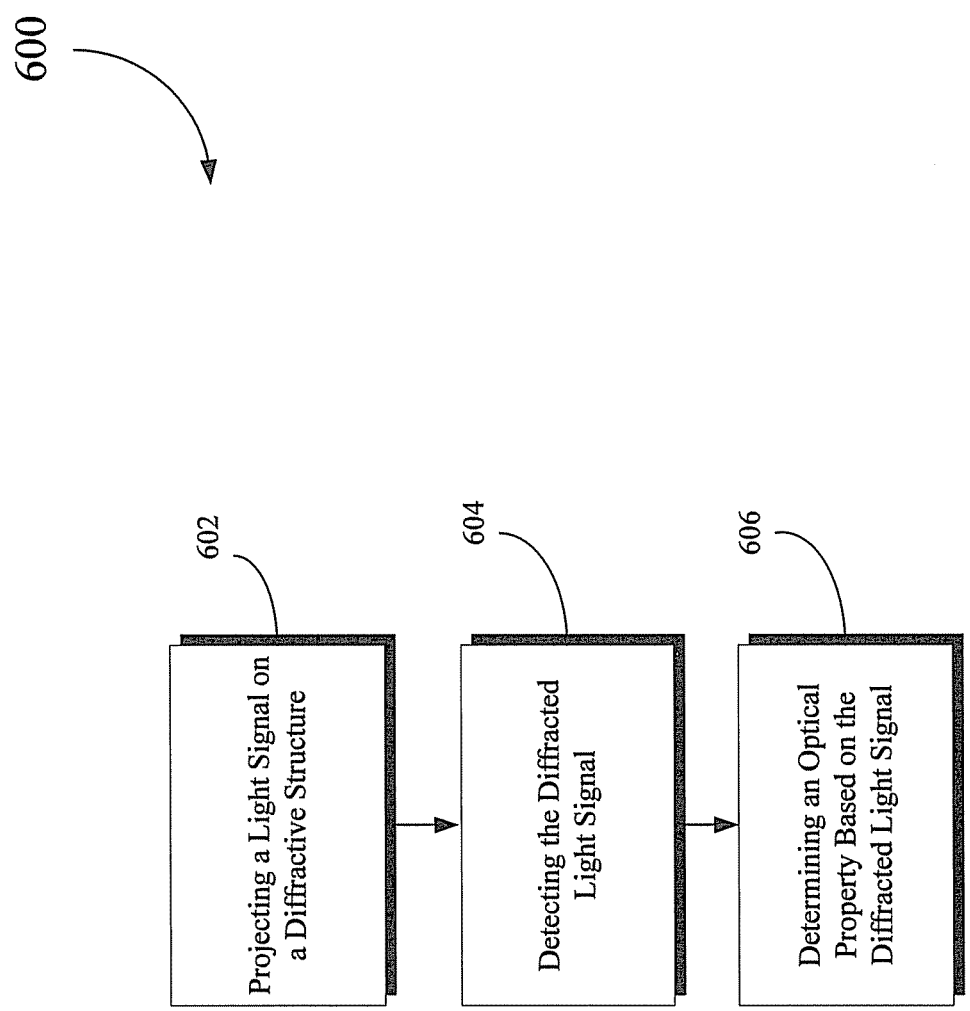
FIG. 6 is a flowchart of an example embodiment of a method for determining an optical property of a set of cells.

Now referring to FIG. 6, an example embodiment of a method 600 for determining an optical property of a set of cells is shown. At step 602, computing unit 116 projects a light signal on a diffractive structure. The diffractive structure may be configured to (i) receive the light signal and (ii) produce a diffractive light signal having plasmon resonance properties and an angular spectrum, the angular spectrum corresponding to the set of cells that are in contact with the diffractive structure. At step 604, computing unit 116 detects the diffracted light signal. And at step 606, computing unit 116 determines the optical property of the set of cells based on the detected diffracted light signal.

It should be understood that although certain steps of method 600 described herein are described as carried out by computing unit 116, this is not necessary. Other computing devices, systems, or units, including integrated or distributed computing units, may be used as well.

At step 602, computing unit 116 projects a light signal on a diffractive structure. In accordance with step 602, computing system 116 may be configured to cause light source 112 to produce light signal 129 for projection on diffractive structure 120. Upon receiving light signal 129, diffractive structure 120 may produce diffracted light signal 130, which may have plasmon resonance properties and an angular spectrum, which corresponds to the set of cells. Further, a light source, light-conditioning unit, and diffractive structure, such as any of those described above and the variations thereof, may be utilized to accomplish the functions described in accordance with step 602.

At step 604, computing unit 116 detects the diffracted light signal. Detection of the diffracted light signal may be accomplished using any of the suitable components described above including, but not limited to a light-collecting unit.

At step 606, computing unit 116 determines the optical property of the set of cells based on the detected diffracted light signal. Determining the optical property of the set of cells based on the detected diffracted light signal may be accomplished using any of the suitable components described above including, but not limited to a light-analyzing unit (which may be integrated in whole or in part with the light-collecting unit). Accordingly, light-analyzing unit 114, perhaps with instructions received from computing unit 116, may be configured to determine an optical property of the set of cells.

Method 600 may optionally and/or additionally include determining an oxygen-saturation level of RBCs based on the optical property determined in accordance with step 606. Such a determination may be performed by computing unit 116, light-analyzing unit 114, and/or a combination thereof. As noted above, oxygen saturation is known to be defined by the following formula: Oxygen Saturation=$HbO_2$/(Hb+ $HbO_2$). Further, dysfunctional hemoglobins, like COHb and MetHb, typically do not support the transport of oxygen and only a few percent of total hemoglobin. As such, an oxygen-saturation level of an individual RBC 111 can be determined based on a measured amount of oxygen-depleted hemoglobin and a measured amount of saturated oxyhemoglobin using the above formula and corresponding detected wavelengths of diffracted light signal.

Further, determining the optical property of the set of cells may involve detecting a respective light-diffracted wavelength for each cell in the set of cells and determining (i) a mean light-diffracted wavelength of the respective light-diffracted wavelengths and (ii) a variance of the respective light-diffracted wavelengths. That is, as noted above, once computing unit 116 has repeated an identification and measurement process for a certain number of cells, their respective measured optical properties may be stored and used to determine a mean and variance of the measured optical properties for the cells over a certain time interval. Further still, the optical property of the set of cells may include an extinction coefficient of the set of cells.

Figure 7:
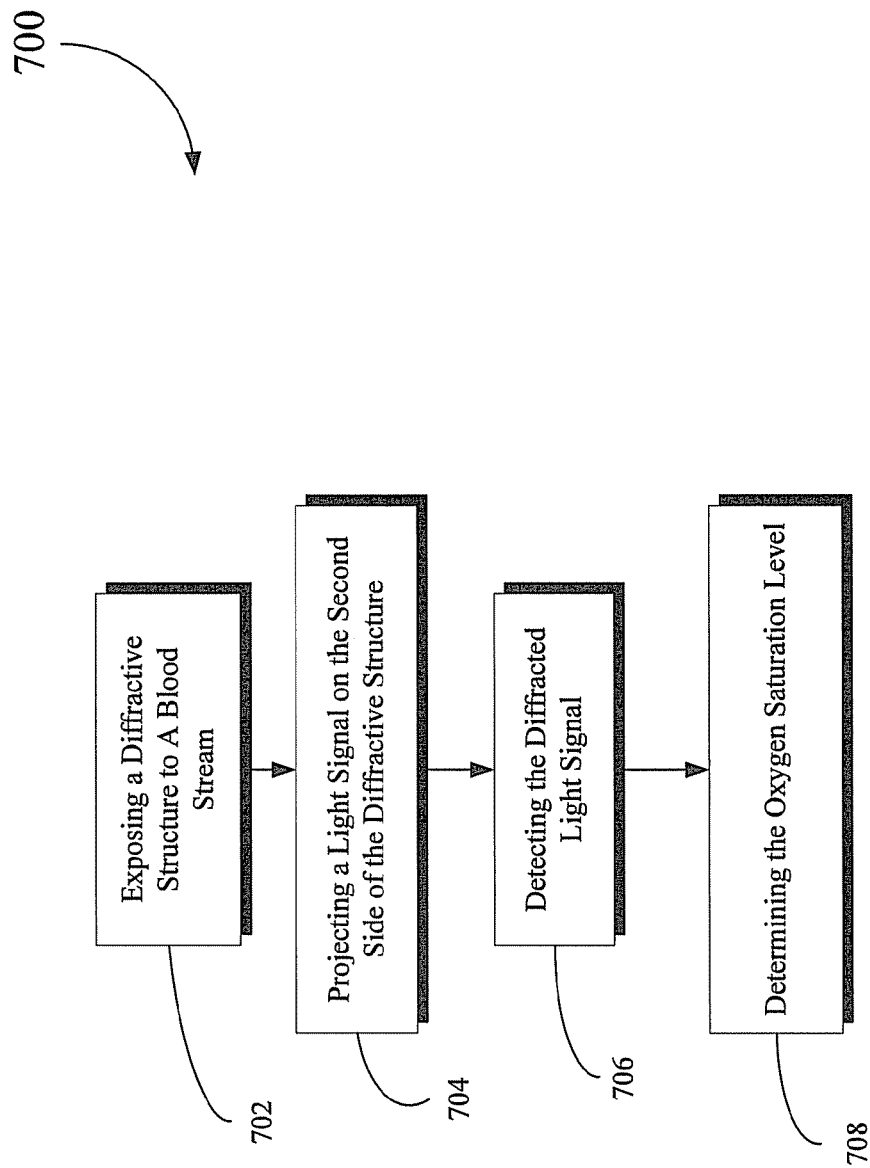
FIG. 7 is a flowchart of an example embodiment of a method for determining an oxygen saturation level of a set of RBCs.

Now referring to FIG. 7, an example embodiment of a method 700 for determining an oxygen saturation level in an individual is shown. At step 702, a first side of a diffractive structure is exposed to a blood stream of the individual such that the first side of the diffractive structure is in contact with a set of red blood cells from the blood stream. The diffractive structure may be configured to (i) receive a light signal on a second side of the diffractive structure and (ii) produce a diffracted light signal having plasmon resonance properties and an angular spectrum, the angular spectrum corresponding to the set of red blood cells. At step 704, computing unit 116 projects the light signal on the second side of the diffractive structure. At step 706, computing unit 116 detects the diffracted light signal. And at step 708, computing unit 116 determines the oxygen saturation level based on the detected diffracted light signal.

It should be understood that although certain steps of method 700 described herein are described as carried out by computing unit 116, this is not necessary. Other computing devices, systems, or units, including integrated or distributed computing units, may be used as well.

At step 702, a first side of diffractive structure is exposed to a blood stream of the individual such that the first side of the diffractive structure is in contact with a set of red blood cells from the blood stream. Step 702 may therefore involve inserting fiber-coupled probe into a blood stream of the individual, so as to expose a first side of diffractive structure 118 to the blood stream of the individual, and thereby putting it in contact with a set of RBCs 111 from the blood stream. The fiber-coupled probe may be placed in the individuals blood stream in any suitable manner. In an embodiment, the fiber-coupled probe may be placed by way of a catheter (placement of the fiber-coupled probe within a catheter is described further above).

Figure 10:
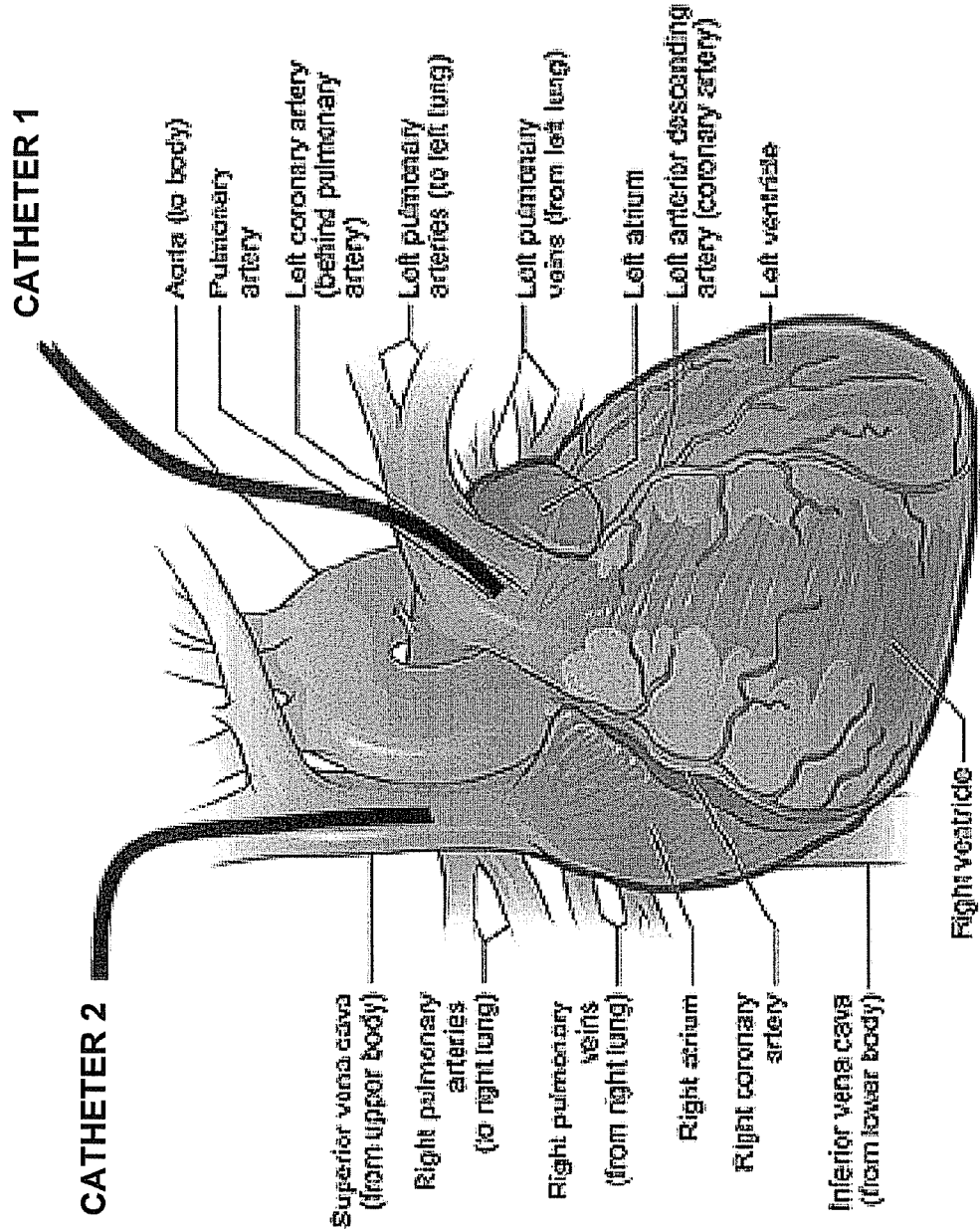
FIG. 10 is a depiction of example catheter placement.

Accordingly, such a catheter may be placed within an individual using any suitable known, or developed, catheter-placement technique or protocol. As one particular example, FIG. 10 depicts the insertion of a first and second catheter (catheter 1 and catheter 2, respectively) into the pulmonary artery and the superior vena cava, respectively. In this way, blood oxygen levels of blood at different stages of the respiratory cycle may be analyzed.

However, it should be understood that the particular placement of catheter 1 and catheter 2 depicted in FIG. 10 is but one example placement of catheters and is depicted for purposes of example and explanation only. Other placement of catheters containing the optical sensors described herein may be desirable and/or possible as well.

At step 704, computing unit 116 projects the light signal on the second side of the diffractive structure. In accordance with step 704, computing system 116 may be configured to cause light source 112 to produce light signal 129 for projection on diffractive structure 120. Upon receiving light signal 129, diffractive structure 120 may produce diffracted light signal 130, which may have plasmon resonance properties and an angular spectrum, which corresponds to the set of cells. Further, a light source, light-conditioning unit, and diffractive structure, such as any of those described above and the variations thereof, may be utilized to accomplish the functions described in accordance with step 604.

At step 706, computing unit 116 detects the diffracted light signal. Detection of the diffracted light signal may be accomplished using any of the suitable components described above including, but not limited to a light-collecting unit.

At step 708, computing unit 116 determines the oxygen saturation level based on the detected diffracted light signal. Determining the oxygen saturation level based on the detected diffracted light signal may involve determining the optical property of the set of cells based on the detected diffracted light signal, which may be accomplished using any of the suitable components described above including, but not limited to a light-analyzing unit (which may be integrated in whole or in part with the light-collecting unit). Accordingly, light-analyzing unit 114, perhaps with instructions received from computing unit 116, may be configured to determine an optical property of the set of cells.

Method 700 may optionally and/or additionally include determining (i) an amount of oxygen-depleted hemoglobin and (ii) an amount of saturated oxyhemoglobin based on the detected diffracted light signal; and determining the oxygen saturation level based on the determined amount of oxygen-depleted hemoglobin and the determined amount of saturated oxyhemoglobin. The amount of oxygen-depleted hemoglobin may be determined based on a first attenuation of the diffracted light signal at a first wavelength associated with oxygen-depleted hemoglobin, and the amount of saturated oxyhemoglobin is determined based on a second attenuation of the diffracted light signal at a second wavelength associated with saturated oxyhemoglobin.

4. Example Computing Unit

Figure 8:
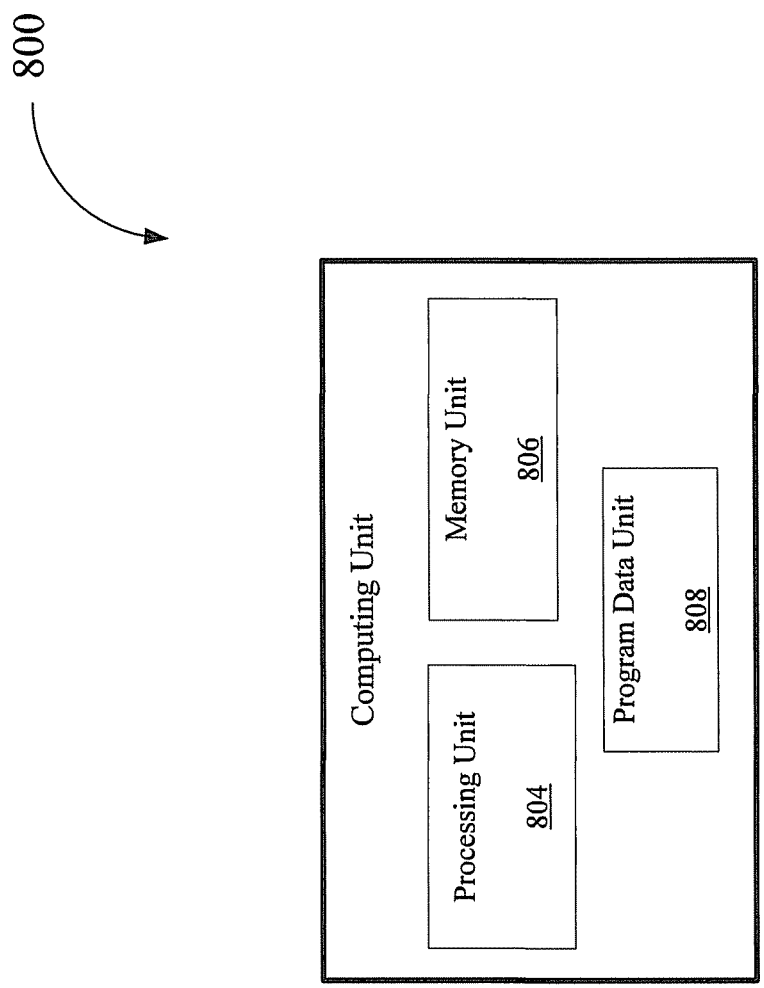
FIG. 8 is a functional block diagram illustrating an example computing unit of FIG. 1.

FIG. 8 illustrates a simplified block diagram 800 of an example computing unit 802. Computing unit 802 includes a processing unit 804, a memory unit 806, and a program data unit 808. Depending on the desired configuration, processing unit 804 can be any type of processor including, but not limited to, a microprocessor (µP), a microcontroller (µC), a digital signal processor (DSP), or any combination thereof. Memory unit 806, which may store software that can be accessed and executed by processing unit 804, for example, can be of any type of memory now known or later developed including but not limited to volatile memory (such as RAM), non-volatile memory (such as ROM, flash memory, etc.), or any combination thereof.

5. Example Non-Transitory Computer Readable Medium

Figure 9:
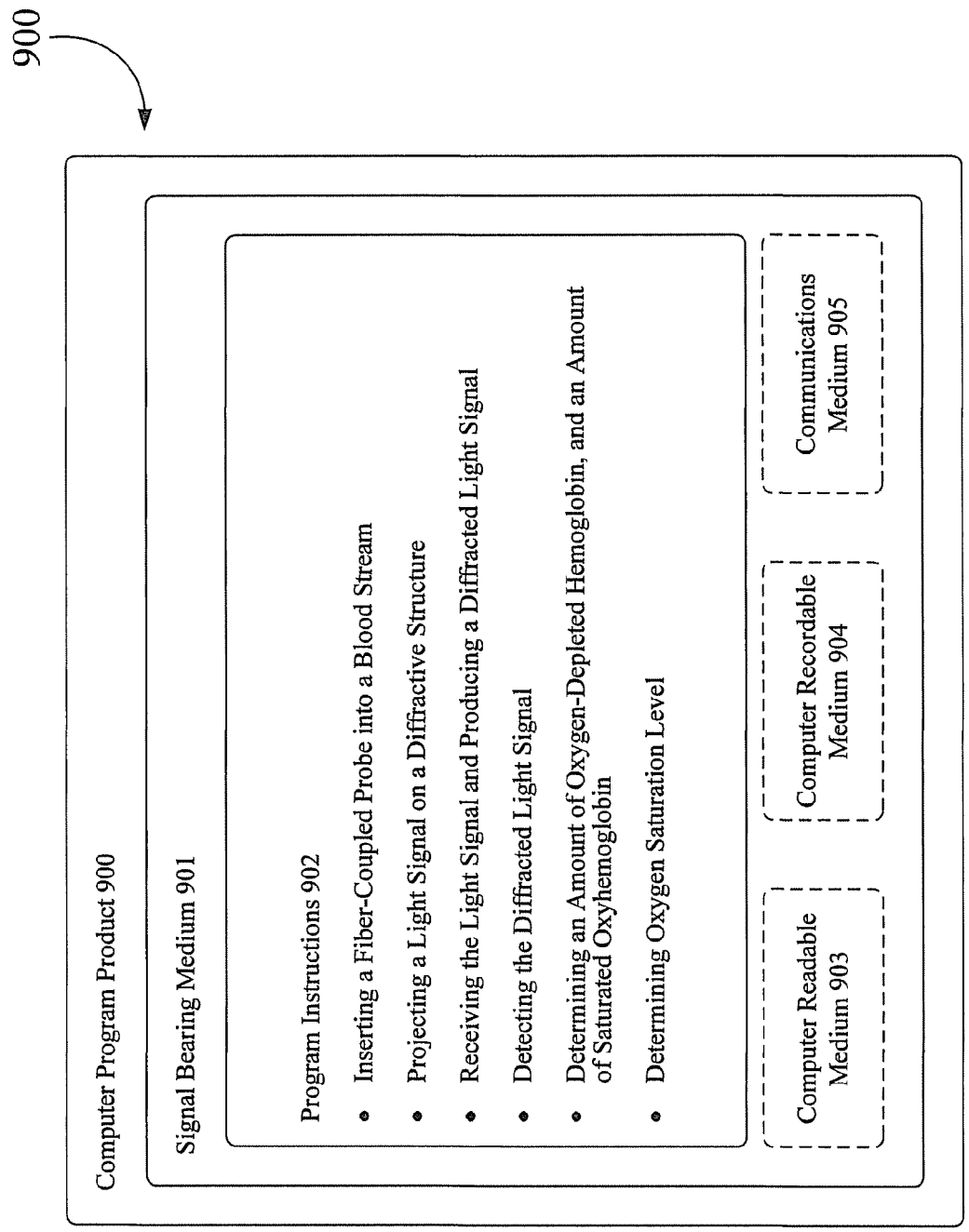
FIG. 9 is a schematic diagram illustrating a conceptual partial view of an example computer program associated with the method of FIG. 6.

In some embodiments, the disclosed methods may be implemented as computer program instructions encoded on a computer-readable storage media in a machine-readable format. FIG. 9 is a schematic illustrating a conceptual partial view of an example computer program product 900 that includes a computer program for executing a computer process on a computing device, arranged according to at least some embodiments presented herein. In one embodiment, the example computer program product 900 is provided using a signal bearing medium 901. The signal bearing medium 901 may include one or more programming instructions 902 that, when executed by one or more processors may provide functionality or portions of the functionality described above with respect to FIGS. 1-7. Thus, for example, referring to the embodiments shown in FIGS. 6 and 7, one or more features of blocks 602, 604, 606, and/or 608, and one or more features of blocks 702, 704, 706, 708, 710, 712, and/or 714 may be undertaken by one or more instructions associated with the signal bearing medium 901.

In some examples, signal bearing medium 901 may encompass a non-transitory computer-readable medium 903, such as, but not limited to, a hard disk drive, a Compact Disc (CD), a Digital Video Disk (DVD), a digital tape, memory, etc. In some implementations, the signal bearing medium 801 may encompass a computer recordable medium 904, such as, but not limited to, memory, read/write (R/W) CDs, R/W DVDs, etc. In some implementations, the signal bearing medium 801 may include a communications medium 905, such as, but not limited to, a digital and/or an analog communication medium (e.g., a fiber optic cable, a waveguide, a wired communications link, a wireless communication link, etc.). Thus, for example, the signal bearing medium 901 may be conveyed by a wireless form of the communications medium 905 (e.g., a wireless communications medium conforming with the IEEE 802.11 standard or other transmission protocol).

The one or more programming instructions 902 may be, for example, computer executable and/or logic implemented instructions. In some examples, a computing device such as the computing unit 116 of FIGS. 1 and 2 may be configured to provide various operations, functions, or actions in response to the programming instructions 902 conveyed to the computing device 102 by one or more of the computer readable medium 903, the computer recordable medium 904, and/or the communications medium 905.

5. Conclusion

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

What is claimed is:

1. An apparatus comprising:
    a diffractive grating configured to interact with at least one test object at a first side of the diffractive grating;
    a light source configured to provide light;
    an optical coupling element coupled to a second side of the diffractive grating;
    a light-conditioning unit configured to guide the light to the optical coupling element to illuminate an area of the second side of the diffractive grating causing the diffractive grating and the at least one test object to exhibit plasmon resonance at respective locations corresponding to the illuminated area, wherein the diffractive grating is further configured to generate a plurality of diffracted light signals having respective intensities representing the magnitude of the plasmon resonance caused at the respective locations; and a light-collecting unit configured to receive the plurality of diffracted light signals.

2. The apparatus of claim 1, further comprising a light detector optically coupled to the light-collecting unit, wherein the light detector is configured to detect the respective intensities of the plurality of diffracted light signals.

3. The apparatus of claim 1, wherein the optical coupling element comprises a prism.

4. The apparatus of claim 1, wherein the diffractive grating is affixed to the light conditioning unit.

5. The apparatus of claim 1, wherein the diffractive grating exhibits one or more diffractive orders.

6. The apparatus of claim 5, wherein the one or more diffractive orders comprises a (−1) diffractive order.

7. The apparatus of claim 1, wherein the plurality of diffracted light signals comprises at least one light signal exhibiting a diffractive order.

8. The apparatus of claim 7, wherein the diffractive order comprises a (−1) diffractive order.

9. The apparatus of claim 1, wherein the at least one test object comprises a blood cell.

10. The apparatus of claim 1, wherein the diffractive grating has a periodic structure with a period that is less than a length of the at least one test object.

11. The apparatus of claim 1, wherein the diffractive grating comprises a plasmon-resonance layer.

12. The apparatus of claim 11, wherein the plasmon-resonance layer comprises silver.

13. The apparatus of claim 12, wherein the grating unit further comprises an adhesion layer coupled to a first side of the plasmon-resonance layer and a protective layer coupled to a second side of the plasmon-resonance layer.

14. The apparatus of claim 13, wherein the adhesion layer comprises chromium and the protective layer comprises silicon dioxide, wherein the adhesion layer couples the diffractive grating to the light-conditioning unit at the second side of the diffractive grating.

15. The apparatus of claim 1, wherein the diffractive structure comprises a grating unit having a non-periodic structure.

16. The apparatus of claim 1, further comprising a catheter that contains the diffractive structure, the light-conditioning unit, and the light-collecting unit.

17. A method comprising:
illuminating an area located at a first side of a diffractive grating, wherein a second side of the diffractive grating interacts with at least one test object, wherein the illuminating causes the diffractive grating and the at least one test object to exhibit plasmon resonance at respective locations corresponding to the illuminated area;

generating, at least in part by the diffractive grating, a plurality of diffracted light signals having respective intensities representing the magnitude of plasmon resonance caused at the respective locations; and detecting the respective intensities of the plurality of diffracted light signals from the respective locations.

18. The method of claim 17, wherein the diffractive grating exhibits at least one diffraction order.

19. The method of claim 18, wherein the at least one diffraction order comprises a (−1) diffraction order.

20. The method of claim 17, wherein the plurality of diffracted light signals exhibit at least one diffraction order.

21. The method of claim 20, wherein the at least one diffraction order comprises a (−1) diffraction order.

22. The method of claim 17, further comprising determining an optical property of the at least one test object at the plurality of locations based on the detected respective intensities of the plurality of diffracted light signals.

23. The method of claim 17, further comprising using the detected respective intensities of the plurality of diffracted light signals to generate an image of the at least one test object.

24. The method of claim 17, wherein the at least one test object is a blood cell.

* * * * *